(12) United States Patent
Wieslander et al.

(10) Patent No.: US 8,197,460 B2
(45) Date of Patent: Jun. 12, 2012

(54) MULTICOMPARTMENT CONTAINER CONTAINING A MEDICAL SOLUTION

(75) Inventors: Anders Wieslander, Lund (SE); Peder Flank, Bjärred (SE); Petra Åhl, Ödåkra (SE)

(73) Assignee: Gambro Lundia AB, Lund (SE)

( * ) Notice: Subject to any disclaimer, the term of this patent is extended or adjusted under 35 U.S.C. 154(b) by 897 days.

(21) Appl. No.: 12/090,225

(22) PCT Filed: Oct. 16, 2006

(86) PCT No.: PCT/SE2006/001167
§ 371 (c)(1),
(2), (4) Date: Sep. 29, 2008

(87) PCT Pub. No.: WO2007/046744
PCT Pub. Date: Apr. 26, 2007

(65) Prior Publication Data
US 2009/0204098 A1    Aug. 13, 2009

Related U.S. Application Data

(60) Provisional application No. 60/596,746, filed on Oct. 18, 2005.

(30) Foreign Application Priority Data

Oct. 17, 2005    (SE) ...................................... 0502365

(51) Int. Cl.
*A61B 19/00*    (2006.01)
*A61M 5/32*    (2006.01)

(52) U.S. Cl. ........................................................ 604/416
(58) Field of Classification Search .............. 604/27–32, 604/82–92, 190, 246–248, 218, 403–416
See application file for complete search history.

(56) References Cited

U.S. PATENT DOCUMENTS

| 4,629,080 A | 12/1986 | Carveth | |
| 5,176,634 A * | 1/1993 | Smith et al. | 604/87 |
| 6,645,191 B1 * | 11/2003 | Knerr et al. | 604/410 |

FOREIGN PATENT DOCUMENTS

| DE | 199 55 578 C1 | | 9/2001 |
| EP | 1 475 067 A1 | | 11/2004 |
| WO | WO 03/068135 | * | 8/2003 |
| WO | WO 03/068135 A1 | | 8/2003 |
| WO | WO 2004/047714 A1 | | 6/2004 |

* cited by examiner

*Primary Examiner* — Tatyana Zalukaeva
*Assistant Examiner* — Philip R Wiest
(74) *Attorney, Agent, or Firm* — Nixon & Vanderhye P.C.

(57) ABSTRACT

A flexible multicompartment container provided for storage and mixing together of a at least a first and a second single solution. Each single solution is stored in a separate compartment (1, 2) of the container. The compartments are separated by means of seals (5, 6) rupturable by manipulation of the container to thereby mix the contents together in a mixing compartment for delivery. The first compartment (1) is filled to a first filling degree, FD1, and the second compartment is filled to a second filling degree, FD2. The first filling degree is larger than the second filling degree. The filling degree in the mixing compartment, FDMC, is larger than the filling degree in the second compartment.

34 Claims, 3 Drawing Sheets

A-A

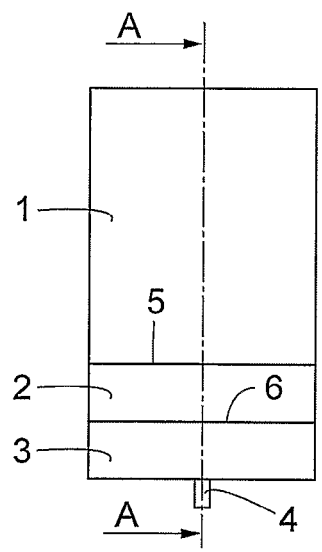
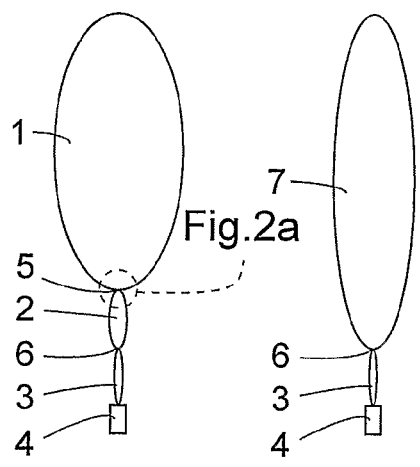
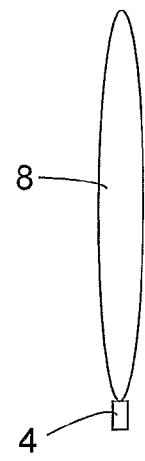
Fig.1a  Fig.1b  Fig.1c  Fig.1d
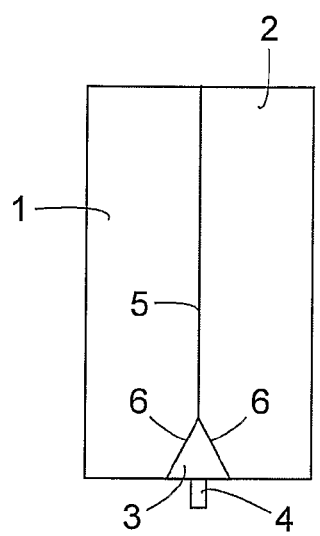
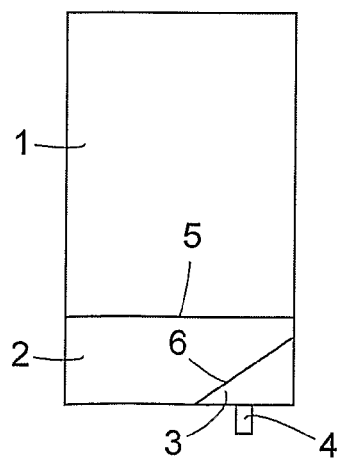
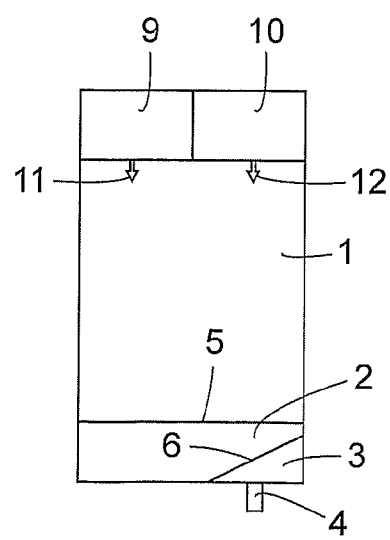
Fig.4a  Fig.5a  Fig.6

MULTICOMPARTMENT CONTAINER CONTAINING A MEDICAL SOLUTION

CROSS REFERENCE TO RELATED APPLICATIONS

This application is a national phase application based on PCT/SE2006/001167, filed Oct. 16, 2006, the content of which is incorporated herein by reference, and claims the priority of Swedish Patent Application No. 0502365-0, filed Oct. 17, 2005, and the benefit of U.S. Provisional Application No. 60/596,746, filed Oct. 18, 2005, the content of both of which is also incorporated herein by reference.

TECHNICAL FIELD OF THE PRESENT INVENTION

The present invention relates to the field of multicompartment containers filled with a medical solution. The medical solution multicompartment containers are configured for storage and mixing of at least a first single solution and a second single solution of the medical solution where the first and the second single solutions are contained in separate compartments of the container and mixed together to a final medical solution before use. The compartments are separated by a peelable seal that may be ruptured by manipulation of the container to mix the first and the second single solution together and deliver the medical solution through an outlet of the multicompartment container.

BACKGROUND OF THE INVENTION

Multicompartment containers for medical solutions are frequently used. Particularly in case the medical solution comprises a mix of one or more single solutions that are incompatible during sterilization or storage and thus have to be separated. For instance a single solution that contains glucose should be kept separate from substances that catalyze the glucose degradation and also kept at a low pH to further stabilize the glucose molecule. Another example is that a single solution containing bicarbonate or phosphate should be kept separated from a single solution containing calcium or magnesium in order to avoid precipitation. A further example is that a diluent and a medicament need to be maintained separate. Still a further example is that a single solution with high pH needs to be maintained separate from a single solution with low pH.

The medical solution used by a patient should always be physiological upon delivery to the patient as well as a medicament should be at correct concentration. For this reason it is of importance that the single solutions are always safely mixed before delivered through an outlet to the patient. In case one of the above-exemplified single solutions is delivered unmixed with the other single solution it may be hazardous to the patient.

The need to keep single solutions of a medical solution separate in compartments of a multicompartment container is recognized in the area of containers for administration of sterile or non-sterile medical solutions in chemical or drug therapies, for nutritional supplements, for apheresis, for parenteral administration, or for renal therapies e.g. hemodialysis, hemodiafiltration, hemofiltration or peritoneal dialysis.

An example of a flexible multicompartment solution container is known from U.S. Pat. No. 5,176,634. U.S. Pat. No. 5,176,634 discloses a container where separate compartments in the container are formed by frangible heat seals. A first compartment contains a liquid diluent; a second compartment contains a powdered medicament, which may be mixed with the liquid diluent by separating the frangible seal dividing the first and the second compartment. Separating of the seal is accomplished by manipulating the container to create pressure on the diluent in the first compartment, which then hydraulically separates the seal between the first and the second compartment allowing the diluent and medicament to be mixed. A third compartment adjacent the second compartment and opposite from the diluent compartment contains an outlet port for dispensing the mixed solution. A seal between the second and the third compartment prevents administration of the contents before mixing of the contents of the first and the second compartment. After mixing, additional manipulation of the container to exert pressure on the contents ruptures the second seal allowing the medicated solution to be dispensed through the port. Where a liquid medicament is used, the relative size between the diluents compartment and the medicament compartment and the placement of the smaller compartment intermediate to the larger compartment and the lower or outlet compartment assures development of hydraulic forces which will rupture the seal between the diluent and medicament compartments before rupture of the second seal with minimal care.

SUMMARY OF THE INVENTION

An object of the present invention is to provide a flexible multicompartment solution container for storing and mixing a medical solution where the container comprises at least a first and a second compartment separated by a first peelable seal, where a first single solution is contained in the first compartment and a second single solution is contained in the second compartment and where the certainty is improved that the first and the second single solutions are mixed before a second peelable seal is opened and the medical solution is ready for delivery.

Another object of the present invention is to provide a flexible multicompartment solution container where it is substantially made difficult to deliver only one of a first and a second single solution to a patient.

Another object of the present invention is to provide a flexible multicompartment solution container where the certainty is improved that a second peelable seal is rupturable only after a first peelable seal has been ruptured.

Such a multicompartment container contains a medical solution which is maintained in separate single solutions in separate compartments in the container until use of the medical solution. Upon use the single solutions are with improved safety mixed before delivery of the medical solution through an outlet of the multicompartment container to a patient.

The concept of "medical solution" as used in this document includes both the possibility that the solution for delivery is a concentrate that is to be diluted before use by the patient and the possibility that the solution for delivery is already of a suitable concentration such that it can be directly used by the patient. The concept "medical solution" also includes the possibility that the solution for delivery is to be mixed with other ingredients before the final medical solution to be fed to the patient is obtained.

One example embodiment of the invention is a flexible multicompartment container that comprises a first, a second and a third compartment. The first compartment contains a first single solution, the second compartment contains a second single solution and the third compartment is empty or mainly empty. With mainly empty is meant that it does not contain any component of the medical solution but may optionally contain an amount of liquid sufficient for sterilizing purposes. The first compartment is separated from the second compartment by means of a first peelable seal. The second compartment is separated from the third compartment by means of a second peelable seal.

The first compartment is filled with the first single solution to a first filling degree. The second compartment is filled with the second single solution to a second filling degree. The first filling degree is larger than the second filling degree. The first filling degree is suitable for rupturing the first peelable seal by manipulation of the container in such a way that pressure is exerted on the contents such that the first peelable seal is ruptured. The second filling degree is not suitable for rupturing neither the first nor the second peelable seal.

When the first peelable seal is ruptured and the first and the second compartment are in fluid communication a mixing compartment is obtained. Mixing of the first and the second single solution takes place in the mixing compartment. The mixing compartment is through the mixing of the first and the second medical solution filled to a third filling degree which is larger than the second filling degree. The third filling degree is suitable for rupturing of the second peelable seal by means of manipulation of the container to exert pressure on the contents and thereby rupture the second seal allowing the medical solution to be dispensed through an outlet port arranged in the third compartment.

According to one embodiment the flexible multicompartment solution container comprises a first main sheet and a second main sheet located opposite to said first main sheet and where the extension of the medical solution container is limited at least substantially by a first, second, third and fourth edge portion, wherein the first edge portion is located opposite said second edge portion and said third edge portion is located opposite said fourth edge portion and where said first and second peelable seal extends across the solution container between said third and fourth edge portion, thereby dividing the solution container into said first, second and third compartments.

In one example embodiment the first edge portion has substantially the same length as the second edge portion. Similarly, according to an embodiment of the invention the third edge portion has substantially the same length as the fourth edge portion. According to an embodiment of the invention the third and fourth edge portions are longer than the first and the second end portions.

In one example embodiment of the invention said first and second sheets are welded to each other along at least said first and second edge portions. To seal the first and second sheets with the help of such welds constitutes a simple manner of fabricating the solution container. It should be noted that according to a further embodiment the first and the second sheets are welded together also along the third and fourth edge portions. Alternatively it is possible that the solution container is made of a tubular material. In this case it is not necessary to seal the solution container along all of said first to fourth edge portions. If the solution container is formed as a tube, the first and second sheets are thus already connected to each other along two of said edge portions. In this case there is therefore no strict boundary between the first and the second sheets along said third and fourth edge portions, since in this case the first and second sheets actually form part of the same tubular piece.

The term "peelable seal" refers to a low strength peelable (rupturable) seal which can be broken by the application of fluid pressure. In a solution storage container the peelable seal is preferably of a strength wherein manually squeezing of the container with liquid and/or entrapped air provides sufficient pressure to rupture the seal.

In this context a compartment is deemed to be filled to 100% when the pressure required to fill the compartment with a liquid solution increases exponentially. The filling degree is herein defined as a percentage of the 100% filled compartment. For handling reasons a compartment is normally not filled to more than 85%, i.e. has a filling degree of 85%.

The configuration and filling of a flexible multicompartment medical solution container according to the present invention is based on the understanding that the filling degree is reciprocally proportional to the force/load needed for rupturing a peelable seal. The explanation for this is that the main determinant for rupturing a peelable seal is an angle $\alpha$ between the two main sheets welded together. According to the present invention this understanding is used to improve the certainty that only by rupturing the first peelable seal between the first and the second compartment it is probable to apply enough pressure to rupture the second peelable seal for delivery of the medical solution to the patient. In this way the certainty is improved that the first and the second single solution of the medical solution is mixed before being delivered to the patient.

Other objects, features, advantages and preferred embodiments of the present invention will become apparent from the following detailed description and claims when taken in conjunction with the enclosed drawings.

BRIEF DESCRIPTION OF THE DRAWINGS

FIG. 1a is a plan view of an example embodiment of a flexible medical solution multicompartment container.

FIG. 1b is a cross-section taken through AA of FIG. 1a. FIG. 1b also includes a reference to FIG. 2a.

FIG. 1c is a cross-section taken through AA of FIG. 1a when a first pealable seal has been ruptured.

FIG. 1d is a cross-section taken through AA of FIG. 1a when a first and a second peelable seal have been ruptured.

FIG. 4a is a plan view of an alternative example embodiment of a medical solution multicompartment container.

FIG. 4b is a diagram showing a filling degree for the first and the second compartment as well as a filling degree of the mixing compartment of the embodiment according to FIG. 4a.

FIG. 5a is a plan view of another alternative example embodiment of a medical solution multicompartment container.

FIG. 5b is a diagram showing a filling degree for the first and the second compartment as well as a filling degree of the mixing compartment of the embodiment according to FIG. 5a.

FIG. 6 is a plan view of an alternative example embodiment of a medical solution multicompartment container containing additional compartments.

DETAILED DESCRIPTION OF THE INVENTION

Figure 2A:
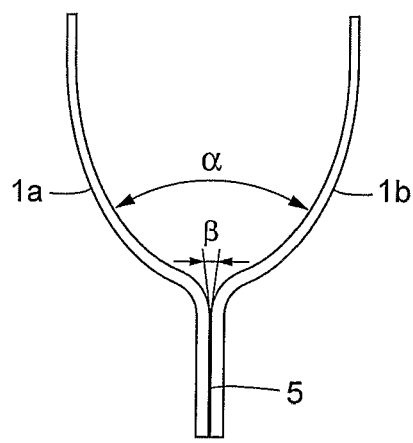
FIG. 2a is an enlarged view of a cross section in FIG. 1b showing an angle $\alpha$ between two main sheets connected together by a peelable seal.

FIG. 1a shows one example embodiment of a multicompartment container for a medical solution. The container comprises a first compartment 1, a second compartment 2 and a third compartment 3. The first compartment 1 contains a first single solution, the second compartment 2 contains a second single solution and the third compartment 3 is empty or mainly empty. The third compartment 3 is provided with an outlet port 4 for outlet of the medical solution to a patient.

The first compartment 1 is separated from the second compartment 2 by means of a first peelable seal 5. The second compartment 2 is separated from the third compartment 3 by means of a second peelable seal 6. The first compartment 1 is filled with the first single solution to a first filling degree, $FD_1$ (not shown). The second compartment 2 is filled with the second single solution to a second filling degree, $FD_2$ (not shown). The first filling degree, $FD_1$, is larger than the second filling degree, $FD_2$.

In the following drawing figures corresponding reference numbers will be used for corresponding features.

FIG. 1b shows a cross-section taken through AA of FIG. 1a. In FIG. 1b it is indicated by way of dimension of the first and the second compartment, respectively, that the first filling degree, $FD_1$, is larger than the second filling degree, $FD_2$, i.e. the degree of filling of the first single solution in the first compartment 1 is larger than the degree of filling of the second single solution in the second compartment 2.

The filling degree, $FD_1$, of the first compartment 1 and the strength of the first peelable seal 5 is chosen in such a way that it is possible to manually apply enough pressure on the first compartment 1 in order to rupture the first peelable seal 5 between the first and the second compartment 1, 2. The filling degree of the second compartment, $FD_2$, is chosen in such a way that it is made considerably difficult to rupture the first 5 or the second 6 peelable seal by manually applying pressure on the second compartment 2.

FIG. 1c shows a cross-section taken through AA of FIG. 1a when the first peelable seal 5 has been ruptured. When the first peelable seal 5 has been ruptured and the first and the second compartment 1, 2 are in fluid communication a mixing compartment 7 is constituted. Mixing together of the first and the second single solution takes place in the mixing compartment 7. The mixing compartment 7 is filled to a third filling degree, $FD_{MC}$, (not shown) which is larger than the second filling degree, $FD_2$.

The filling degree of the mixing compartment, $FD_{MC}$ and the strength of the second peelable seal 6 is chosen in such a way that it is possible to manually apply enough pressure on the mixing compartment 7 in order to rupture the second peelable seal 6 between the mixing compartment 7 and the third compartment 3. In one example embodiment of the invention the strength of the first and the second peelable seal 5, 6 is more or less equal.

FIG. 1d shows a cross-section taken through AA of FIG. 1a when the first 5 and subsequently the second 6 peelable seal has been ruptured. At this stage the multicompartment container includes an outlet compartment 8 containing the medical solution ready for delivery. The medical solution is delivered to the patient via the outlet port 4. The outlet port 4 may be openable for delivery of the medical solution by an opening means such as a valve member, a peelable seal or a frangible pin.

FIG. 2a shows an enlarged part of FIG. 1b comprising a first and a second main sheet 1a, 1b connected together by means of a peelable seal 5. Between the first and the second main sheet is formed an angle $\alpha$. This angle $\alpha$ is related to the filling degree in the first compartment, $FD_1$, in such a way that a higher filling degree renders an increased angle $\alpha$ between the first and the second main sheet 1a, 1b. The actual determinant for the rupturing of the first peelable seal 5 is a crack-propagation angle $\beta$. The crackpropagation angle $\beta$, is the angle between the first and the second main sheet 1a, 1b at the point where the rupture starts. The crackpropagation angle $\beta$ depends on the specific material and the specific production process. Thus, a higher filling degree in the first compartment, $FD_1$ increases the angle $\alpha$ between the first and the second sheet 1a, 1b and thereby increases the probability/simplicity for exceeding the crackpropagation angle $\beta$ and rupturing the peelable seal 5 when manually squeezing the first compartment 1.

Figure 2B:
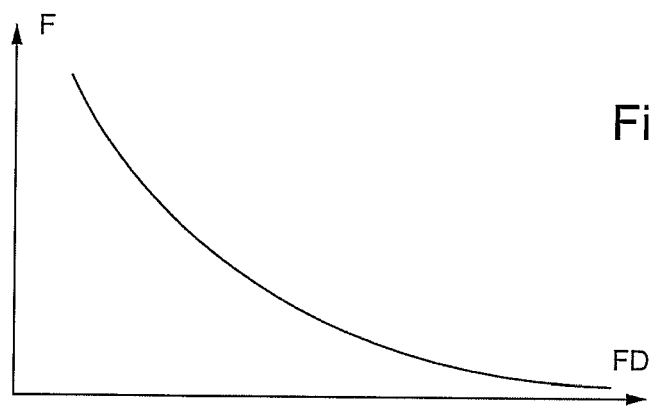
FIG. 2b is a diagram illustrating the ratio between an opening force and a filling degree.

FIG. 2b shows a diagram illustrating the ratio between an opening force, F and a filling degree, FD. A higher filling degree, FD, requires a lower opening force, F.

According to the present invention the following ratio between the first, second and third filling degree is required:

$$FD_1 > FD_2$$

and $$FD_{MC} > FD_2$$

where
$FD_1$=filling degree of the first compartment 1
$FD_2$=filling degree of the second compartment 2
$FD_{MC}$=filling degree of the mixing compartment 7

For handling reasons the first filling degree, $FD_1$, should be larger than 40%, the second filling degree, $FD_2$, less than 45% and the third filling degree, $FD_{MC}$, larger than 10%.

A multicompartment container according to the present invention would typically be configured sufficiently large for containing 0.5 to 20 litres of medical solution. Large volumes of medical solution are especially of interest when performing longlasting treatments, e.g. nightly treatments such as continuous peritoneal dialysis or in connection with intensive care.

Below are disclosed two example embodiments of multicompartment containers and how their respective filling degrees are determined.

Figure 3:
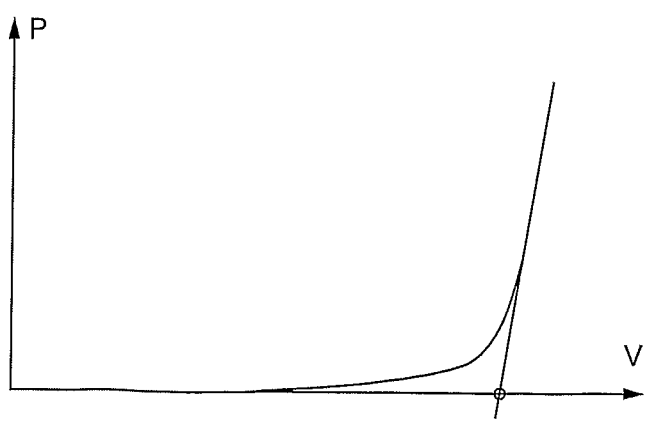
FIG. 3 is a diagram showing an example measurement for determining a 100% filling of a compartment. The Y-axis of the diagram shows pressure and the X-axis shows volume. A 100% filling degree is determined to be where a normal crosses the X-axis.

A 100% filling degree is determined for each of the first 1, second 2 and mixing 7 compartment in the multicompartment container. FIG. 3 shows a diagram illustrating a measurement for determining a 100% filling of a compartment. The compartment is considered to be filled to 100% when a pressure, P, required to fill the compartment with a liquid solution to a volume, V, increases exponentially as shown in FIG. 3. The volume corresponding to a compartment filled to 100% is determined by drawing a normal to the exponential curve and reading the value of the volume, V, where it crosses the x-axis.

For handling reasons a corresponding compartment is normally not filled to more than 85%, i.e. such a compartment has a filling degree of 85%.

Figure 4B:
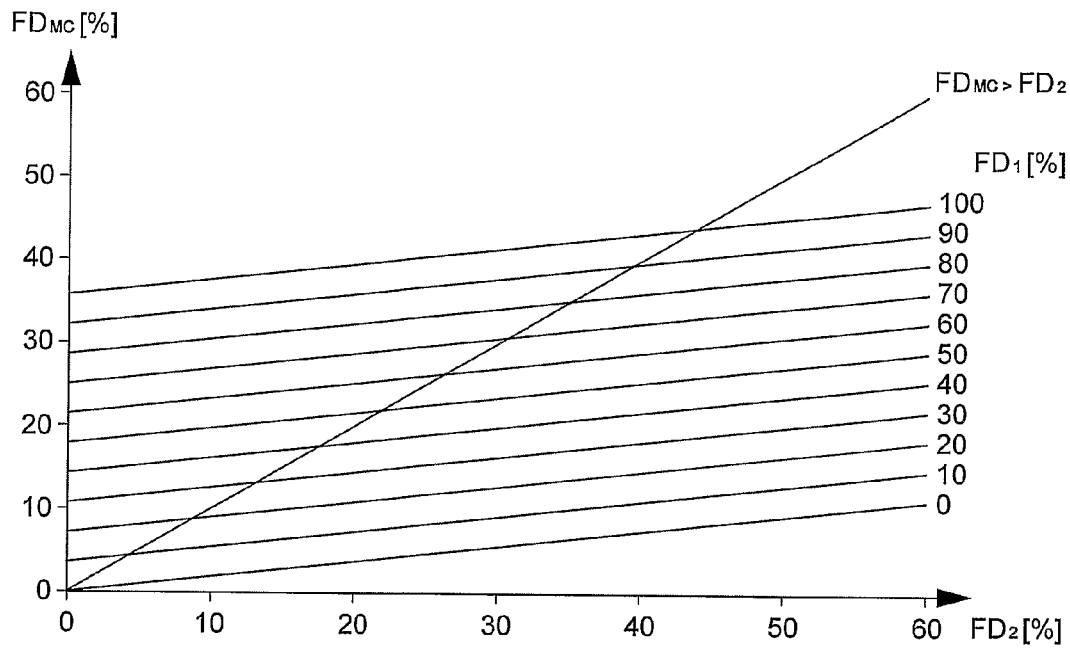
Figure 5B:
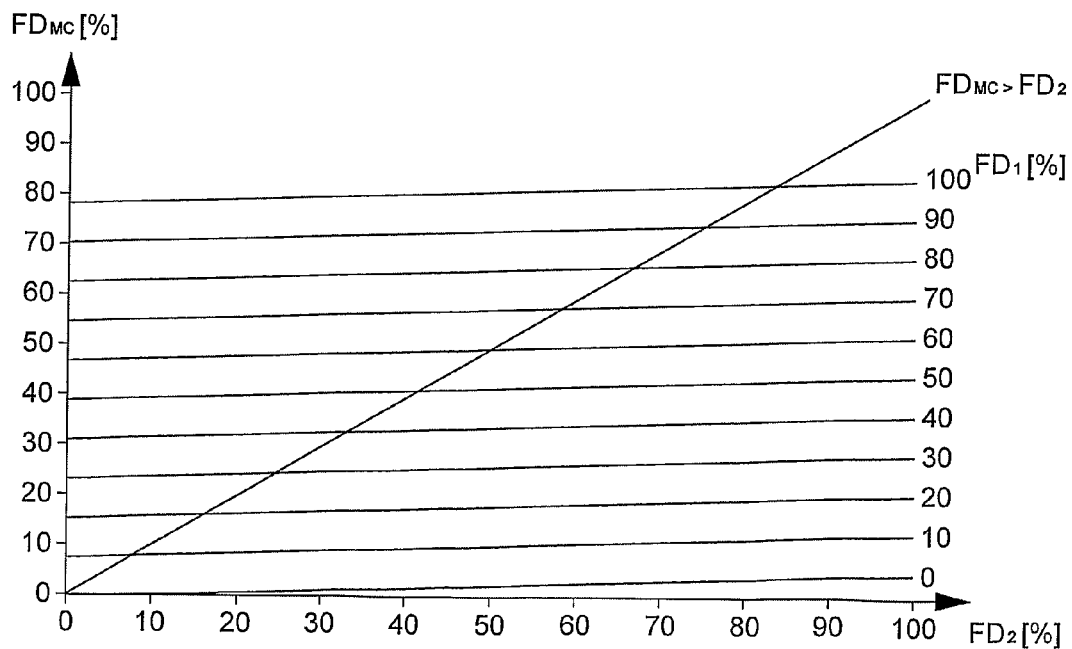

The resulting data, i.e. the determination of the respective volume, V, considered to fill a compartment to 100%, is used for calculating data providing basis for the diagram shown in FIGS. 4b and 5b. For these calculations the following formula is applied.

$$FD_{MC} = (FD_1 \times V_1 + FD_2 \times V_2)/V_{MC}$$

where
$FD_{MC}$=filling degree of the mixing compartment 7
$FD_1$=filling degree of the first compartment 1
$FD_2$=filling degree of the second compartment 2
$V_1$=volume of solution corresponding to 100% filling degree of the first compartment 1
$V_2$=volume of solution corresponding to 100% filling degree of the second compartment 2

$V_{MC}$=volume of solution corresponding to 100% filling degree of the mixing compartment 7

The resulting diagrams shown in FIGS. 4b and 5b are providing basis for determining the preferred values of the respective filling degrees, $FD_1$, $FD_2$ and $FD_{MC}$.

FIG. 4a shows one example embodiment of a multicompartment container for a medical solution where the first 1 and the second 2 compartment is substantially of the same dimension. The multicompartment container shown in FIG. 4a is related to the diagram shown in FIG. 4b. In the diagram in FIG. 4b the filling degree of the first compartment, $FD_1$, is plotted in ten intervals from 0-100%. The X-axis shows the filling degree of the second compartment, $FD_2$, and the Y-axis shows the filling degree of the mixing compartment, $FD_{MC}$.

In the diagram a continuous line is drawn. The area above this continuous line indicates the relevant first and second filling degrees fulfilling the requirement $FD_{MC} > FD_2$.

In one embodiment of the invention the multicompartment container 1 shown in FIG. 4a contains a total volume of 500 ml of medical solution. The first compartment 1 contains 425 ml of a first single solution and the second compartment 2 contains 75 ml of a second single solution.

In one example embodiment of the invention the multicompartment container shown in FIG. 4a has a filling degree in the first compartment, $FD_1$, of 70%-100% and a filling degree in the second compartment, $FD_2$, of 10%-40%. In another example embodiment the filling degree in the second compartment, $FD_2$, is 10%-35%.

In one example embodiment of the invention the multicompartment container shown in FIG. 4a has a filling degree in the first compartment, $FD_1$, of 80%-90% and a filling degree in the second compartment, $FD_2$, of 30%-40%.

In one example embodiment of the invention the multicompartment container shown in FIG. 4a has a filling degree in the first compartment, $FD_1$, of 85%, a filling degree in the second compartment, $FD_2$, of 29% and a filling degree in the mixing compartment, $FD_{MC}$, of 36%.

In one example embodiment of the invention the multicompartment container shown in FIG. 4a has a first compartment 1 containing a single medical solution containing acetic acid and a second compartment 2 containing a single medical solution containing glucose. This example embodiment of the invention is suitable for use in connection with hemodialysis treatment.

FIG. 5a shows one example embodiment of the invention where the multicompartment container has a first compartment 1 which, in relation to the second compartment 2, is large and a second compartment which in relation to the first compartment is small.

FIG. 5b shows a diagram for the container configuration according to FIG. 5a. The diagram corresponds to the diagram described in connection with FIG. 4b.

In one example embodiment of the invention the multicompartment container 1 shown in FIG. 5a contains a total volume of 5000 ml of medical solution. The first compartment 1 contains 4850 ml of a first single solution and the second compartment 2 contains 150 ml of a second single solution.

One example embodiment of the invention the multicompartment container shown in FIG. 5a has a filling degree in the first compartment, $FD_1$, of 70%-100% and a filling degree in the second compartment, $FD_1$, of 10%-40%.

In one example embodiment of the present invention the multicompartment container has a filling degree in the first compartment, $FD_1$, of 80%, a filling degree in the second compartment, $FD_2$, of 33% and a filling degree in the mixing compartment, $FD_{MC}$, of 64%.

In one example embodiment of the present invention the multicompartment container shown in FIG. 5a contains a single medical solution containing acid, glucose, calcium and magnesium and the second compartment 2 contains a single solution containing alkaline bicarbonate and sodium. This example embodiment of the invention is suitable for use in connection with intensive care treatment.

FIG. 6 shows a multicompartment container similar to the multicompartment container shown in FIG. 5a but with a fourth and a fifth compartment 9, 10. In this example embodiment of the invention the first compartment contains a single medical solution containing acid, calcium, magnesium and sodium and the second compartment contains a single solution containing alkaline bicarbonate and the container contains 2000 ml medical solution. The fourth and the fifth compartments 9, 10 contain glucose in different concentrations, e.g. in the concentration of 50%. A first breakable pin 11 is arranged between the fourth 9 and the first 1 compartment and a second breakable pin 12 is arranged between the fifth 10 and the first 1 compartment. The first and the second breakable pin 11, 12 is arranged to allow fluid communication between the fourth compartment 9 and the first compartment 1 and between the fifth compartment 10 and the first compartment 1, respectively. The use of the content in any of, or both of, the fourth and fifth compartments is optional when mixing the medical solution. This example embodiment of the invention is suitable for use in connection with peritoneal dialysis treatment.

In one example embodiment of the present invention the third compartment 3 is containing water or saline for sterilization purposes. By containing water or saline in the third compartment sterility of the multicompartment container may be assured at a lower temperature, i.e. at about 120 degrees Celcius instead of at about 185 degrees Celcius.

In one example embodiment of the present invention the multicompartment container is made from a non-PVC film.

The invention is not limited to the described embodiments but may be varied and modified within the scope of the following claims.

The invention claimed is:

1. A flexible multicompartment container containing a medical solution, comprising at least first, second, and third compartments, wherein the first compartment is filled with a first single solution and the total volume of fluid in the first compartment is at a first filling degree, $FD_1$, and the second compartment is filled with a second single solution and the total volume of fluid in the second compartment is at a second filling degree, $FD_2$, said first and second compartments being separated by a first peelable seal, and wherein a mixing compartment is provided when the first and second compartments are arranged in fluid communication with each other by rupturing the first peelable seal, the first filling degree, $FD_1$, being larger than the second filling degree, $FD_2$, and the total volume of fluid in the mixing compartment is at a filling degree in the mixing compartment $FD_{MC}$, which is larger than the filling degree in the second compartment, $FD_2$ and wherein the fluids in the first, second and mixing compartments are substantially entirely liquid.

2. A multicompartment container according to claim 1, wherein the first filling degree, $FD_1$, is larger than 40%, the second filling degree, $FD_2$, is less than 45%, and the filling degree in the mixing compartment, $FD_{MC}$, is larger than 10%.

3. A multicompartment container according to claim 1, wherein the first filling degree $FD_1$ is at least 70% and the second filling degree $FD_2$ is no more than 40%.

4. A multicompartment container according to claim 1, wherein the first filling degree $FD_1$ is 70-100% and the second filling degree $FD_2$ is 10-40%.

5. A multicompartment container according to claim 4, wherein the second filling degree $FD_2$ is 10-35%.

6. A multicompartment container according to claim 1, wherein the first filling degree $FD_1$ is 80-90% and the second filling degree $FD_2$ is 30-40%.

7. A multicompartment container according to claim 1, wherein the first filling degree $FD_1$ is 85%, the second filling degree $FD_2$ is 29%, and the filling degree in the mixing compartment, $FD_{MC}$, is 36%.

8. A multicompartment container according to claim 1, wherein first filling degree $FD_1$ is 80%, the second filling degree $FD_2$ is 33%, and the filling degree in the mixing compartment, $FD_{MC}$, is 64%.

9. A multicompartment container according to claim 1, wherein the mixing compartment of the multicompartment container is sufficiently large to contain at least 500 ml of the medical solution, wherein the medical solution includes the first and second single solutions.

10. A multicompartment container according to claim 9, wherein, prior to the rupturing of the first peelable seal, the first compartment contains approximately 425 ml of the first single solution and the second compartment contains approximately 75 ml of the second single solution.

11. A multicompartment container according to claim 1, wherein the multicompartment container is sufficiently large to contain at least 2000 ml of the medical solution.

12. A multicompartment container according to claim 1, wherein the multicompartment container is sufficiently large to contain at least 5000 ml of the medical solution.

13. A multicompartment container according to claim 12, wherein the multicompartment container contains approximately 4850 ml of the first single solution and approximately 150 ml of the second single solution, wherein the medical solution includes the first and second single solutions.

14. A multicompartment container according to claim 1, wherein the third compartment is separated from the mixing compartment by a second peelable seal, said third compartment having an outlet port.

15. A multicompartment container according to claim 14, wherein the medical solution is of such a concentration that the solution is suitable to be delivered through the outlet port to a patient without being further diluted, and the medical solution includes the first and second single solutions.

16. A multicompartment container according to claim 14, wherein the medical solution is diluted before being delivered through the outlet port to a patient.

17. A multicompartment container according to claim 14, wherein the first filling degree, $FD_1$, is sufficient to rupture the first peelable seal and the filling degree, $FD_2$, in the mixing compartment, $FD_{MC}$, is sufficient to rupture the second peelable seal.

18. A multicompartment container according to claim 17, wherein the first and second peelable seals have substantially equal strength.

19. A flexible multicompartment container containing a medical solution, said flexible multicompartment container comprising at least first, second, and third compartments, wherein the first compartment is filled with a first single solution and the total volume of fluid in the first compartment is at a first filling degree, $FD_1$, and the second compartment is filled with a second single solution and the total volume of fluid in the first compartment is at a second filling degree, $FD_2$, the first and second compartments being separated by a first peelable seal, and wherein a mixing compartment is provided when the first and second compartments are arranged in fluid communication with each other by rupturing the first peelable seal, said mixing compartment being separated from the third compartment by a second peelable seal, the first filling degree, $FD_1$, being larger than the second filling degree, $FD_2$, and a total volume of fluid in the mixing compartment is at a filling degree $FD_{MC}$, which is larger than the filling degree in the second compartment, $FD_2$, said first filling degree, $FD_1$, being sufficient to rupture the first peelable seal and the filling degree in the mixing compartment, $FD_{MC}$, being sufficient to rupture the second peelable seal, and wherein the fluids in the first, second and mixing compartments are substantially entirely liquid.

20. A multicompartment container according to claim 19, wherein the first and second peelable seals have substantially equal strength.

21. A flexible container comprising:
a first compartment containing a first liquid which fills the first compartment and a total volume of fluid in the first compartment is at a first filling degree, $FD_1$;
a second compartment separated from the first compartment by a first seal, wherein a second liquid fills the second compartment and a total volume of fluid in the second compartment is at a second filling degree, $FD_2$, which is less than $FD_1$;
a mixing compartment which is formed by combining the first and second compartments, and the mixing compartment is filled, in response to the rupturing of the first seal, with a liquid mixture including the first liquid and the second liquid, wherein the total volume of fluid in the mixing compartment is at a filling degree $FD_{MC}$, which is greater than $FD_2$, wherein the fluids in the first, second and mixing compartments are substantially entirely liquid, and
a second seal separating the mixing compartment from a passage to an outlet of the container.

22. The flexible container of claim 21 wherein the second seal is in fluid communication with the second compartment and is not in fluid communication with the first compartment, while the first seal is sealed.

23. The flexible container of claim 21 wherein the container is a multicompartment container of medical liquids, and the first and second liquids are each medical liquids.

24. The flexible container of claim 21 wherein the mixing compartment includes the first and second compartments.

25. The flexible container of claim 21 wherein a force required to rupture the second peelable seal is greater than a maximum force applied by a person compressing with only his hands the second compartment prior to the rupturing of the first container and while only the second liquid is in the second compartment.

26. The flexible container of claim 25 wherein the force required to rupture the second peelable seal is less than the maximum force applied by the person compressing with only his hands the mixing compartment after the rupture of the first peelable seal and while the liquid mixture is in the mixing compartment.

27. The flexible container of claim 21 wherein the second seal is a peelable seal.

28. The flexible container of claim 21 wherein a minimum force required to rupture the first seal is substantially the same as a minimum force required to rupture the second seal.

29. The flexible container of claim 21 wherein the first filling degree $FD_1$ is at least 70% and the second filling degree $FD_2$ is no more than 40%.

30. The flexible container of claim 21 wherein the first filling degree $FD_1$ is in a range of 70 percent (%) to 100% and the second filling degree $FD_2$ is in a range of 10% to 40%.

31. The flexible container of claim 30 wherein the second filling degree $FD_2$ is in a range of 10% to 35%.

32. The flexible container of claim 21 wherein the first filling degree $FD_1$ is in a range of 80% to 90% and the second filling degree $FD_2$ is in a range of 30% to 40%.

33. The flexible container of claim 21 wherein second filling degree $FD_2$ is no greater than 29%, and the mixed filling degree, $FD_{MC}$, is at least 36%.

34. The flexible container of claim 21 wherein the first filling degree $FD_1$ is at least 80%, the second filling degree $FD_2$ is no greater than 33%, and the mixed filling degree, $FD_{MC}$, is at least 64%.

* * * * *